(12) United States Patent
Dinarello

(10) Patent No.: US 7,741,276 B2
(45) Date of Patent: Jun. 22, 2010

(54) USE OF INTERLEUKIN-18 INHIBITORS TO INHIBIT TUMOR METASTASIS

(75) Inventor: Charles Dinarello, Boulder, CO (US)

(73) Assignee: Ares Trading S.A. (CH)

( * ) Notice: Subject to any disclaimer, the term of this patent is extended or adjusted under 35 U.S.C. 154(b) by 258 days.

(21) Appl. No.: 11/825,548

(22) Filed: Jul. 6, 2007

(65) Prior Publication Data

US 2008/0003216 A1  Jan. 3, 2008

Related U.S. Application Data

(63) Continuation of application No. 10/048,916, filed as application No. PCT/IL00/00419 on Jul. 17, 2000, now abandoned.

(30) Foreign Application Priority Data

Jul. 22, 1999 (IL) ..................................... 131047

(51) Int. Cl.
*A61K 38/00* (2006.01)
*A61K 35/12* (2006.01)
(52) U.S. Cl. ....................................... 514/2; 424/277.1
(58) Field of Classification Search ................... None
See application file for complete search history.

(56) References Cited

FOREIGN PATENT DOCUMENTS

| EP | 0 850 952 A | 7/1998 |
|---|---|---|
| WO | 98/41232 A | 9/1998 |
| WO | 99/09063 A | 2/1999 |

OTHER PUBLICATIONS

Ared et al Immunological review, vol. 223, p. 20-38, 2008.*
Kim et al JBC, vol. 277, p. 10998-03, 2002.*
Vidal-Vanaclocha et al PNAS, vol. 97, p. 734-739, Jan. 2000.*
Okahara et al, Cancer Research vol. 54 p. 3233-3236, 1994.*
Iwasaki et al, J Immunther, suppl 1" S52-60, Mar.-Apr. 2002, abstract.*
Nakata et al, Anticancer Res., vole 19 p. 4131-8, 1999, abstract.*
Anasagasti et al. Hepatology 25:840-846 (1997).
Bani et al. J. Natl. Cancer Inst. 83:119-123 (1991).
Bazan et al. Nature 379(6566):591 (1996).
Bertorneu et al. Clin. Exp. Metastasis 11:243-250 (1993).
Burrows et al. Cancer Res. 51:4768-4775 (1991).
Chirivi et al. Cancer Res. 53:5051-5054 (1993).
Dinarello et al. J. Leukocyte Biol. 63(6):658-664 (1998).
Fantuzzi et al. Blood 91:2118-2125 (1998).
Freedman et al. Science 249:1030-1033 (1990).
Garofalo et al. Cancer Res. 55:414-419 (1995).
Kohn et al. Cancer Res., 55(9):1856-1862 (1995).
Lauri et al. Clin. Exp. Metastasis 8:27-32 (1990).
Malik et al. Eur. J. Cancer 26:1031-1034 (1990).
Martin-Padura et al. Cancer Res. 51:2239-2241 (1991).
Mendoza et al. J. Cell Physiol. 174:322-330 (1998).
Miyake et al. Res. Comm. Chem. Pathol. Pharmacol. 71:293-307 (1991).
Nicolson et al. Nature 255:230-232 (1975).
Novick et al. Immunity 10:127-136 (1999).
Okahara et al. Cancer Res. 54:3233-3236 (1994).
Okamura et al. Nature 378:88-91 (1995).
Orosz et al. Int. J. Cancer 60:867-871 (1995).
Orosz et al. J. Exp. Med. 177:1391-1398 (1993).
Pages et al. Immunology Letters 68(1):135-139 (1999).
Puren et al. J. Clin. Invest 101(3):711-724 (1998).
Rice et al. Science 246:1303-1306 (1989).
Simmons et al. Blood 80(2):388-95 (1992).
Tsutsui et al. J. Immunol. 159(8):3961-3967 (1997).
Vidal-Vanaclocha et al. Cancer Res. 54:2667-2672 (1994).
Vidal-Vanaclocha et al. Cytokine 9(11):897 (1997).
Vidal-Vanaclocha et al. Hepatology 18:328-339 (1993).
Vidal-Vanaclocha et al. J. Natl. Cancer Inst. 88:198-205 (1996).
Vidal-Vanaclocha et al. PNAS 97(2):734-739 (2000).
Nakata et al., Anticancer Res. 19:4131-8, 1999.
Ligo et al., Cytokine 25:36-44, 2004.
Freshney, Culture of Animal Cells, A Manual of Basic Technique, Alan R. Liss, Inc., 1983, New York, p4.
Dermer, Bio/Technology, 1994, vol. 12, p. 320.
Gura, Science, vol. 278, p. 1041-1042, 1997.

* cited by examiner

*Primary Examiner*—Larry R. Helms
*Assistant Examiner*—Lei Yao
(74) *Attorney, Agent, or Firm*—Nixon Peabody LLP

(57) ABSTRACT

Use of IL-18 inhibitors in tumor metastasis is disclosed.

1 Claim, 5 Drawing Sheets

USE OF INTERLEUKIN-18 INHIBITORS TO INHIBIT TUMOR METASTASIS

This application is a Continuation application of a co-pending U.S. application Ser. No. 10/048,916, filed Jul. 9, 2002, which is U.S. National Stage Entry under 35 U.S.C. §371 of International Application No. PCT/IL00/00419, filed Jul. 17, 2000, which claims benefit of Israeli application No. 131047, filed on Jul. 22, 1999.

FIELD OF THE INVENTION

The present invention relates to tumor metastasis and means to inhibit it. More specifically, the invention relates to prevention of tumor metastasis by inhibiting the production and/or action of interleukin-18 (IL-18).

BACKGROUND OF THE INVENTION

The adhesion of circulating cancer cells to capillary endothelium is a critical step in the genesis of metastasis (1,2). Vascular cell adhesion molecule-1 (VCAM-1), a member of the immunoglobulin superfamily, mediates the adhesion of hematopoietic cells and activated leukocytes to proinflammatory cytokine-activated endothelial cells (3-5). However, the adhesive function of VCAM-1 may be usurped by animal and human cancer cells to potentiate experimental metastatic spread (6).

For example, IL-1β and TNF-α are known to potentiate the metastasis of VLA-4-expressing melanoma cells in lung tissue by a mechanism that involves the up-regulation of VCAM-1 expression by endothelial cells (7-9). It has also been demonstrated that IL-1 and TNF-α significantly contribute to hepatic colonization of B16M cells both in normal and lipopolysaccharide-treated mice (7,8,10-20). In addition, mannose receptor-mediated hepatic sinusoidal endothelium (HSE) cell activation involves autocrine IL-1β-mediated HSE cell expression of VCAM-1, leading to increased B16M cell adhesion and metastasis (21). It was also shown that IL-1β-activated HSE cells release VLA-4-stimulating factors, which potentiate B16M cell adhesion to HSE cells (11). Thus, IL-1β induces VCAM-1 expression and VLA-4-stimulating factor release from HSE cells, which may confer upon them an ability to create a prometastatic microenvironment for certain intrasinusoidally-arrested VLA-4-expressing cancer cells.

However, blocking IL-1β and TNF-α led to only a partial metastasis abrogation, indicating that other factors either compensating for their absence, or acting via alternative pathways are also involved. Furthermore, most of metastasizing cancer cells and the target tissues are unable to produce these pro-inflammatory cytokines. Moreover, endotoxin or mannose receptor ligand concentration usually does not sufficiently increase to induce proinflammatory cytokine release. Hence, the multiple mediators that evoke VCAM-1 upregulation and its involvement during capillary transit of cancer cells are not well characterized.

IL-18 (IFNγ-inducing factor) is a novel cytokine that shares structural features with the IL-1 family of proteins (22) and functional properties with IL-12 (23). It has been reported that IL-18 production from Kupffer cells activates both TNF-α and FAS ligand-mediated hepatotoxic pathways in endotoxin-induced liver injury (24). More recently, it has been revealed that IL-18 also possesses proinflammatory properties by direct stimulation of gene expression and synthesis of TNF-α from $CD3^+/CD4^+$ and natural killer cells with subsequent production of IL-1β and IL-8 from the $CD14^+$ population, thereby revealing an unexpected pivotal position of IL-18 in the cytokine hierarchy (25). However, its possible role in cancer metastasis has not yet been elucidated.

An interleukin-18 binding protein (IL-18BP) was purified from urine by chromatography on IL-18 beads, sequenced, cloned and expressed in COS7 cells. IL-18BP abolished IL-18 induction of interferon-γ (IFN-γ), IL-8 and activation of NF-κB in vitro. Administration of IL-18BP to mice abrogated circulating IFN-γ following LPS. Thus, IL-18BP functions as an inhibitor of the early Th1 cytokine response. IL-18BP is constitutively expressed in the spleen, belongs to the immunoglobulin superfamily and has limited homology to the IL-1 type II receptor. Its gene was localized on human chromosome 11q13 and no exon coding for a transmembrane domain was found in an 8.3 kb genomic sequence. Several Poxviruses encode putative proteins highly homologous to IL-18BP, suggesting that viral products may attenuate IL-18 and interfere with the cytotoxic T-cell response (28 and WO 99/09063). As described more particularly in WO 99/09063, IL-18BP and muteins, fused proteins, functional derivatives, active fractions or circularly permutated derivatives and mixtures thereof are capable of binding to IL-18 and/or capable of modulating the activity of IL-18 and/or capable of blocking the activity of IL-18.

SUMMARY OF THE INVENTION

The present invention provides for the use of inhibitors of IL-18 production and/or action in the preparation of medicaments to inhibit tumor metastasis.

Inhibitors of IL-18 production are e.g. inhibitors of caspase-1.

The inhibitors of IL-18 action are selected from antibodies against IL-18, antibodies against any of the IL-18 receptor subunits, inhibitors of the IL-18 receptor signaling pathway, antagonists of IL-18 which compete with IL-18 and block the IL-18 receptor, and IL-18BPs, muteins, fused proteins, functional derivatives, active fractions or circularly permutated derivatives thereof which bind IL-18.

Preferably the inhibitors used are IL-18BPs, or a mutein, fused protein, functional derivative, active fraction or circularly permutated derivative thereof which has the same activity as IL-18BP.

Pharmaceutical compositions for inhibition of IL-18 production and/or action to inhibit tumor metastatis are also provided by the present invention.

Another way of inhibiting IL-18 production and/or action, in order to inhibit tumor metastatis, is the introduction into the body of an expression vector comprising the coding sequence for an IL-18 production and/or action inhibitor, such as an IL-18BP.

µg/ml anti-mouse IL-18 antibody before B16M-CM. The percentage of B16M cells adhered to HSE substrate was calculated as relative value with respect to the initial number of added cells. In addition, the culture supernatants were recovered before adhesion to determine IL-1β and TNF-α concentration by ELISA. Data represent the mean ±SD of 4 separate experiments, each in sextuplicate (n=24). The augmentation of B16M cell adhesion to B16M-CM-treated HSE and of IL-1β or TNF-α production with respect to untreated HSE (*P<0.01) were statistically significant according to the Student's two-tailed, unpaired t-test. There were non-statistically significant changes in IL-1β or TNF-α production and in adhesion of B16M cells to HSE cells when these were treated with ICEi or anti-IL-18 antibody in the absence of B16M-CM (data not shown).

Figure 3A:
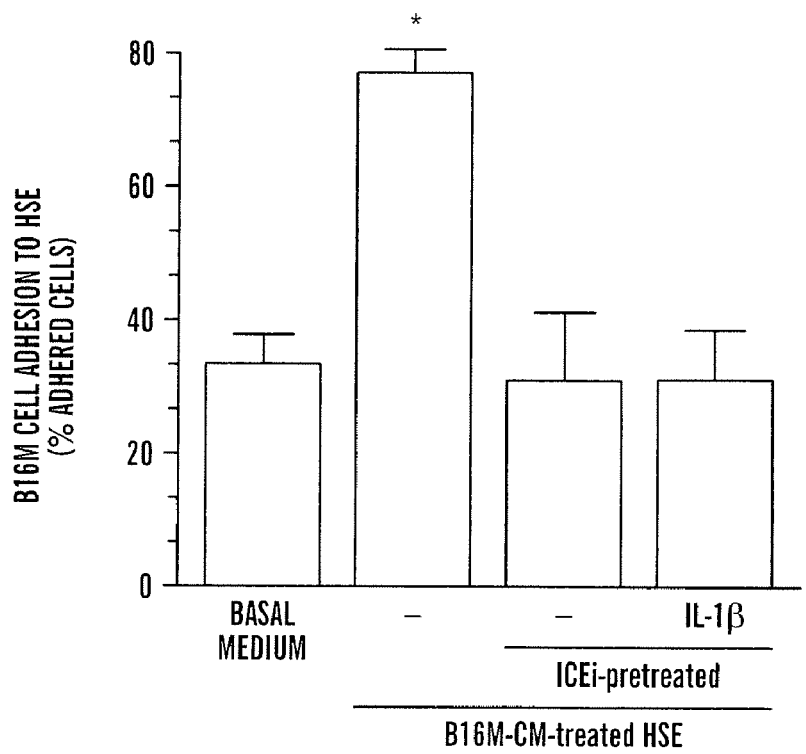
Figure 3B:
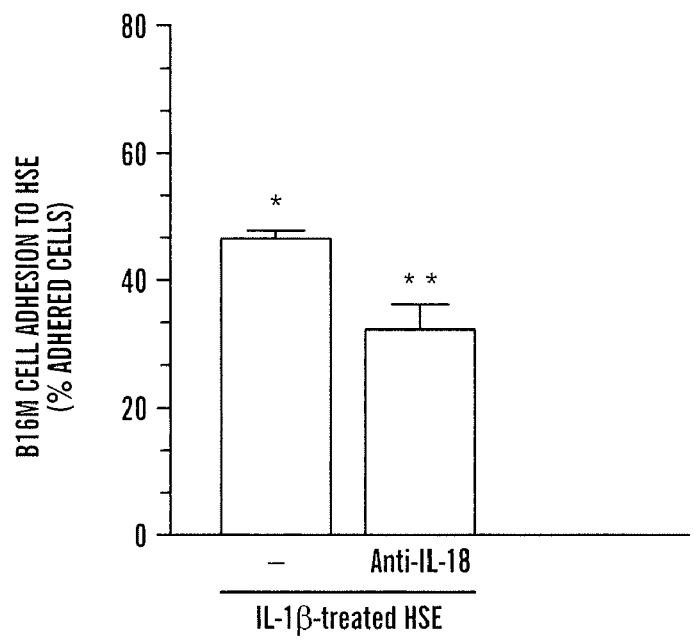
Figure 3C:
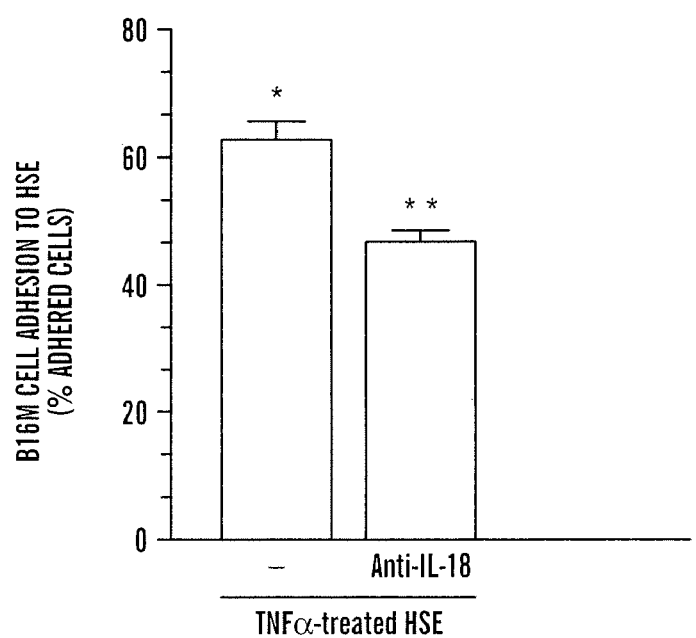

FIG. 3. Effect of ICEi on B16M cell adhesion to B16M-CM-treated HSE in vitro. HSE cells were incubated with basal medium or B16M-CM for 8 h. Some HSE cells received 10 µM ICEi for 18 h before B16M-CM. In addition, 1 ng/ml recombinant murine IL-1β was also added to some HSE cells together with B16M-CM for 8 h. In other experiments, HSE cells received 1 ng/ml murine IL-1β or 100 pg/ml TNF-α for 6 h, and 10 µg/ml rabbit anti-mouse IL-18 polyclonal antibody was added or not 1 h before the cytokine treatment. Non-specific IgG polyclonal antibody was also added to untreated and cytokine-treated HSE cells. Then, HSE cells were washed and BCEFCF-AM-labeled B16M cells were added and washed again 8 min later. The percentage of B16M cells adhered to HSE substrate was calculated as relative value with respect to the initial number of added cells. The results represent the mean ±SD of three separate experiments, each in sextuplicate (n=18). Differences in the degree of adhesion with respect to untreated HSE (*) and to IL-1β or TNF-α-treated HSE (**) were statistically significant (P<0.01), according to the Student's two-tailed, unpaired t-test. Non-statistically significant changes in adhesion of B16M cells to other ICEi-treated control HSE which additionally received or not 1 ng/ml murine IL-1β for 8 h (data not shown).

Figure 4:
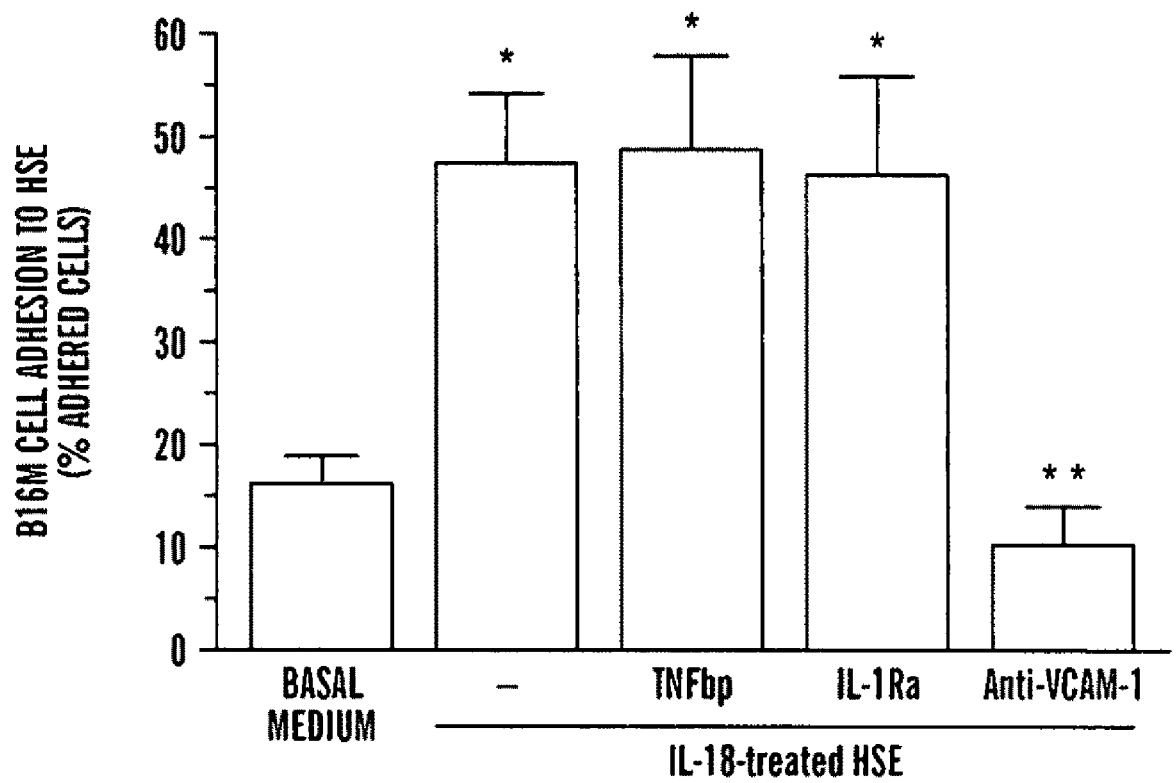

FIG. 4. In vitro B16M cells adhesion to IL-18-treated HSE. HSE cells were incubated with 1 ng/ml recombinant murine IL-18 for 6 hours. In some experiments, 10 µg/ml TNF-sRp55 or 100 ng/ml IL-1Ra was added 10 min before IL-18. In other experiments, 10 µg/ml anti-VCAM-1 antibody or a similar concentration of non-specific anti-mouse IgG was added to HSE cells 30 min before B16M cells. Then, B16M cell adhesion percentage was determined as described hereinbelow in the examples. The results represent the mean ±SD of three separate experiments, each in sextuplicate (n=18). Differences in the degree of adhesion with respect to basal medium-treated HSE (*) and to IL-18-treated HSE (**) were statistically significant (P<0.01), according to the Student's two-tailed, unpaired t-test.

DETAILED DESCRIPTION OF THE INVENTION

Several proinflammatory cytokines, including interleukin (IL)-1β and tumor necrosis factor-alpha (TNF-α), promote the adhesion of cancer cells to endothelial cells, thereby leading to metastatic spread of tumors. These proinflammatory cytokines promote adhesion and metastasis probably by inducing the vascular cell adhesion molecule-1 (VCAM-1). The present invention shows that treatment of primary cultured murine HSE cells with conditioned medium (CM) from B16 melanoma (B16M) cell cultures (B16M-CM) promotes the adhesion between B16M and HSE cells in vitro. B16M-CM also induces the production of IL-1β and TNF-α by HSE cells in vitro. However, it has not been clearly demonstrated that tumor metastasis is indeed mediated by IL-1β and TNF-α.

The present invention shows that B16M-CM induces the production of IL-18 by HSE cells and that IL-18 is the cytokine contributing to increased adhesion of B16M cells to HSE cells. IL-18 enhances adhesion by activating VCAM-1 expression in HSE cells without the involvement of TNF-α or IL1β. Incubation of HSE cells with a specific caspase-1 inhibitor (10 µM, 18 h) completely abrogates B16M-CM-induced adhesiveness without decreasing TNF-α production, and the effect is not reverted by addition of mouse IL-1β. Addition of anti-murine IL-18 antibody to HSE cells prevents B16M-CM-induced adhesiveness, without interfering with B16M-CM-induction of IL-1β and TNF-α. Similarly, the recently cloned IL-18 binding protein (IL-18BP) also prevents B16M-CM-induced adhesiveness of B16M to HSE cells in vitro. Inhibitors of TNF-α and IL-1β such as the p55 soluble TNF-receptor or the IL-1 receptor antagonist were unable to reverse this IL-18-induced adhesion. Thus, the present invention provides inhibitors of IL-18 production and action as tools to inhibit tumor metastasis. Inhibitors of IL-18 production include inhibitors of caspase-1. Inhibitors of IL-18 action are selected from a group consisting from antibodies directed against IL-18, antibodies directed against any one of the two known IL-18 receptor subunits, inhibitors of the IL-18 receptor signalling pathway, antagonists of IL-18, which compete with IL-18 and block the IL-18 receptor and IL-18 binding proteins, which bind IL-18 and block its biological activity.

The present invention relates to the possible role of IL-18 in the proinflammatory cytokine-mediated upregulation of VCAM-1 expression, its possible interaction with other cytokines and means to prevent this induction of VCAM-1. It was found in accordance with present invention that IL-18 is operating in the initiation of proinflammatory events leading to VCAM-1 upregulation in the hepatic sinusoidal wall and hence, facilitating cancer cell adhesion and metastasis. Primary cultured mouse HSE cells treated with B16M-CM were used as a cancer cell-dependent endothelial cell activation model in order to explore the role of B16M cell-induced IL-18 on the mechanism of B16M cell adhesion to HSE by a VCAM-1-dependent mechanism. The specific role of IL-18 was examined under conditions of specific IL-1 receptor-blockade with the use of IL-1Ra, mature IL-1β and IL-18 secretion inhibition using an irreversible IL-1 converting enzyme inhibitor (ICEi), TNF-blockade using the p55 TNF-soluble receptor (TNF-sR p55) and IL-18 function blockade using anti-IL-18 antibodies and IL-18 binding protein. In addition, B16M cells were intrasplenically injected in ICE$^{-/-}$ and IL-1β$^{-/-}$ mice. The low metastasis density observed in the deficient mice as compared with normal controls suggests the involvement of IL1β and possibly IL-18 in the prometastatic role of inflammation (Table 1).

The in vitro experiments carried out show that IL-18 production accounts for the HSE adhesion-stimulating effects induced by supernatants derived from B16M cells. Since VCAM-1 upregulation accounts for all adhesion-stimulating activity of B16M-CM-treated HSE, the data indicate that IL-18 mediates expression of VCAM-1 from cytokine-induced HSE. Furthermore, antibodies to IL-18 decreased B16M-CM-inhibited cell adhesion without affecting the production of TNF-α and IL-1β from HSE cells. Therefore, production of IL-1β and TNF-α in HSE cells was IL-18-independent and did not contribute to adhesion. Conversely, neither TNF-sR p55 nor IL-1Ra were able to inhibit adhesion increase in IL-18-treated HSE cells, confirming that neither autocrine TNF-α nor IL-1β accounted for IL-18-induced HSE adhesiveness.

The results in HSE cells are in contrast to those obtained in other cellular systems, as for example non CD14+ human blood mononuclear cells (25), where IL-18 induced IL-1β via TNF-α production. It is likely that an HSE-specific proinflammatory cytokine hierarchy exists in which TNF-α and IL-1β are independent from IL-18 control, but are using IL-18 as a downstream mediator of VCAM-1 upregulation.

Unlike murine HSE cells, B16M cells did not express the IL-18 gene as checked by RT-PCR, and incubation with ICEi for 18 h did not abrogate cytokine- and adhesion-stimulating activities of B16M-CM on HSE cells. However, local production of IL-18 may influence B16M cell behavior during its transit or arrest in the hepatic microvasculature. An additional finding was that B16M cell incubation with 1 ng/ml murine IL-18 for 6 h increased by 2-fold their adhesion to untreated HSE, and addition of anti-VCAM-1 antibody to HSE decreased IL-18-mediated adhesion by 80%, suggesting that VCAM-1/VLA-4 interaction was involved. Similarly, B16M cells receiving the supernatant from B16M-CM-treated HSE for 6 h also significantly ($P<0.01$) increased by 2-fold their adhesion to HSE by VCAM-1-dependent mechanism and anti-IL-18 antibody abolished this adhesion-stimulating effect.

The findings in accordance with the present invention suggest that IL-18 is a new link between hepatic release of proinflammatory cytokines and metastasis development. Its production from tumor-activated HSE cells determines two complementary mechanisms involved in the regulation of melanoma cell adhesion to HSE cells: an autocrine mechanism in HSE, which controls TNF-α/IL-1β-mediated VCAM-1 upregulation, and a paracrine mechanism in B16M cells, which upregulates melanoma cell VLA-4, potentiating their VCAM-1-dependent adhesion capacity. This simultaneous molecular upregulation of both cell adhesion counterparts make highly valuable the cancer-capillary endothelial cell interaction pathway.

The IL-18-induced adhesion of B16M cells is abrogated by inhibitors of IL-18 production and/or action. Inhibitors of IL-18 production include inhibitors of caspase-1. Inhibitors of IL-18 action are selected from a group consisting from antibodies directed against IL-18, antibodies directed against any one of the two known IL-18 receptor subunits, inhibitors of the IL-18 receptor signalling pathway, antagonists of IL-18, which compete with IL-18 and block the IL-18 receptor, and IL-18 binding proteins, which bind IL-18 and block its biological activity.

In addition to the direct use of inhibitors of IL-18 production and/or action, the present invention also contemplates introduction into cells where the IL-18 production and/or action inhibiting effect is desired. For this purpose a system for specific introduction of, e.g. the DNA encoding an IL-18BP into the cells is necessary. Several possibilities for doing this are known in the art. For example, a suitable vector carrying the above DNA may be introduced into cells, the vector being capable of effecting the insertion of the DNA into the cells in a way such that the DNA is expressed in the cells. Delivery methods into cells are described among others, e.g. in U.S. Pat. No. 5,910,487, WO99/29349, and others.

Pharmaceutical compositions in accordance with the invention for the inhibition of IL-18 production and/or action are those which comprise, as active ingredient an inhibitor selected from a caspase-1 inhibitor, an antibody against IL-18, an antibody against any of the IL-18 receptor subunits, an inhibitor of the IL-18 receptor signaling pathway, an antagonist which competes with IL-18 and blocks the IL-18 receptor and IL-18BP or a mutein, fused protein, functional derivative, active fraction or circularly permutated derivative thereof which has the same activity.

The terms mutein, fused protein, functional derivative, active fraction and circularly permutated derivative have the same meaning as in WO 99/09063.

Antibodies to IL-18 and IL-18BPs are the preferred active ingredients of the pharmaceutical compositions.

The pharmaceutical compositions may also comprise conventional carriers, excipients and other ingredients known in the art, depending on their manner of application, i.e. injection, oral or any other way known in the art.

The particular dosage will depend on the manner of application, the body weight of the patient and other factors and will in any case be determined by the physician.

Having now described the invention, the same will be more readily understood through reference to the following examples that are provided by way of illustration and are not intended to be limiting of the present invention.

EXAMPLES

Reagents:

Rat anti-mouse IgG and rat anti-mouse VCAM-1 monoclonal antibody were obtained from Serotec Ltd. (Oxford, England). Recombinant murine IL-1β was obtained from R&D System Inc. (Minneapolis, Minn.). Recombinant human IL-1 receptor antagonist (IL-1Ra was a kind gift from The Upjohn Co., Kalamazoo, Mich.) and human p55 TNF soluble receptor (TNFsR p55) was a kind gift from Serono Inc., Norwell, Mass. IL-1β converting enzyme inhibitor (ICEi) was obtained from Alexis Co. (San Diego, Calif.). Recombinant murine IL-18 and rabbit anti-mouse IL-18 polyclonal antibody IgG was purchased from PeproTech EC Ltd. (London, UK). IL-18 binding protein (IL-18BP) was produced as described (28).

Culture of B16M cells. B16M cells were cultured, maintained and passaged as previously described (11). B16M conditioned medium (B16M-CM) was prepared as follows: $5\times10^5$ cells were plated in a 25 cm² T-flask and cultured for 24 h. After which, cells were cultured for an additional period of 24 h in 5 ml serum-free medium (final cellular density of $6\times10^4$ cells/cm²). Supernatants were collected, diluted 3:1 in fresh serum-free medium and passed through a 0.22 Ïm filter.

Cytokine Analysis. Release of cytokines from primary cultured HSE cells and B16M cells was measured using specific ELISA kits based on anti-mouse IL-1β and TNF-α monoclonal antibodies, as suggested by the manufacturer (R&D Systems, Minneapolis, Minn.).

Example 1

Quantitative B16M Cell Adhesion to Primary HSE Cultures

HSE was separated from syngeneic mice, identified and cultured as previously described (26). B16M cells were labeled with 2',7'-bis-(2-carboxyethyl)-5,6-carboxyfluorescein-acetoxymethylester solution (BCECF-AM, Molecular Probes, Eugene, Oreg.) as reported (16). Then, $2\times10^5$ cells/well were added to 24-well-plate cultured HSE and 8 min later, wells were washed three times with fresh medium. The number of adhering cells was determined using a quantitative method based on a previously described fluorescence measurement system (16). In some experiments, HSE cells were pre-incubated with B16M-CM for several hours before addition of B16M cells.

Example 2

Hepatic Metastasis Assay

Wild-type, IL-1β$^{-/-}$ and ICE$^{-/-}$ male C57BL/6J mice were generated as previously described (27). Six- to eight-week-old mice, housed five per cage, were used. Hepatic metastases were produced by the intrasplenic injection into anesthetized mice (Nembutal, 50 mg/kg intraperitoneal) of 3×10$^5$ viable B16 melanoma cells suspended in 0.1 ml Hanks' balanced salt solution. Mice were killed under anesthesia on the 10th day after the injection of cancer cells. Liver tissues were processed for histology. Densitometric analysis of digitalized microscopic images was used to discriminate metastatic B16M from normal hepatic tissue and the liver metastasis density, which is the number of metastases per 100 mm$^3$ of liver (based on the mean number of foci detected in fifteen 10×10 mm$^2$ sections per liver), was calculated using previously described stereological procedures (17).

Example 3

Figure 1:
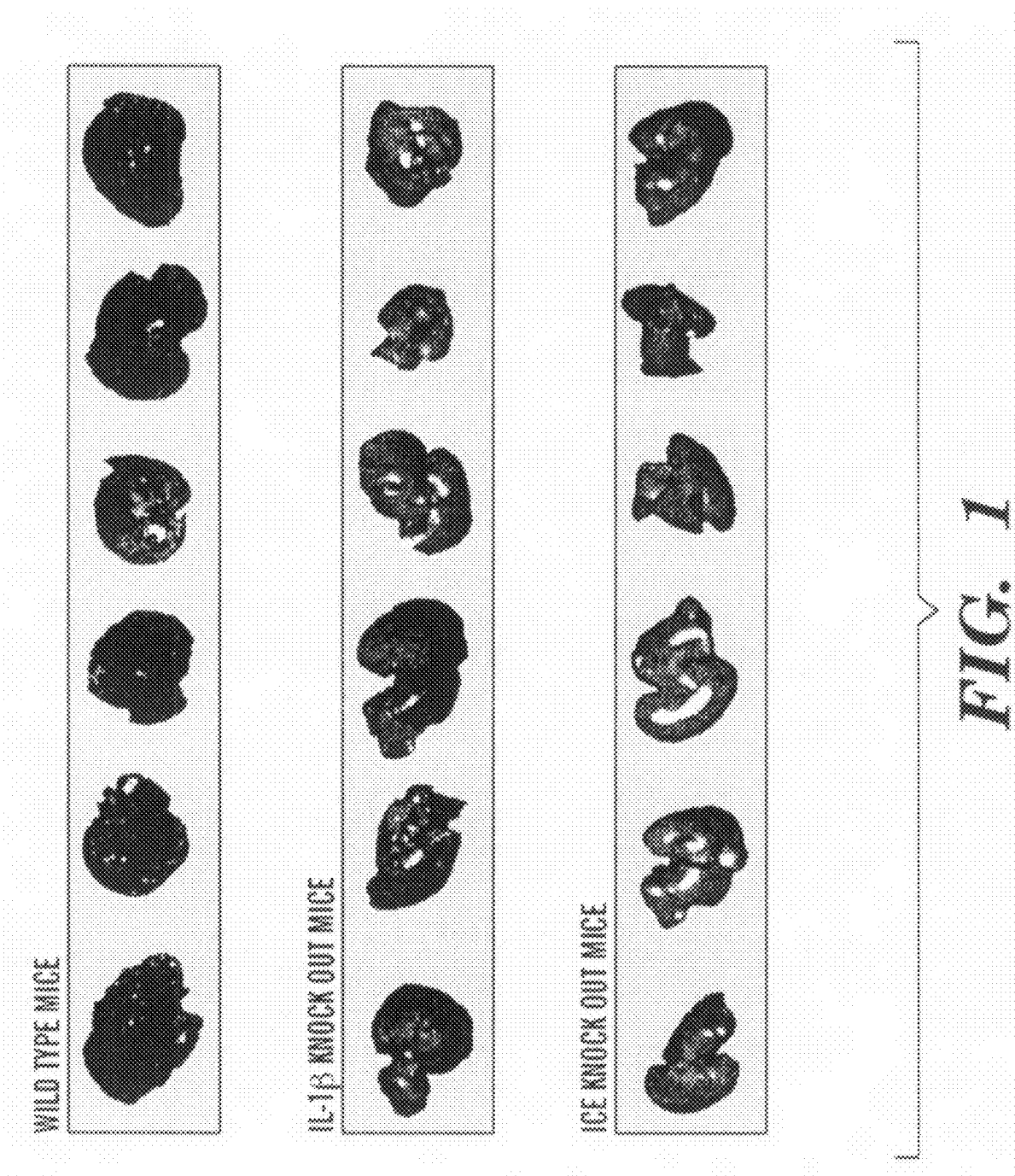
FIG. 1. Experimental hepatic colonization after intrasplenic B16M cell injection in the wild type, IL-1β$^{-/-}$ AND ICE$^{-/-}$ mice. Livers were removed on day 10 after B16M cell injection and fixed in phosphate buffered saline with 10% formaldehyde. Almost all experimental metastases (black melanotic nodules) were eradicated from IL-1β$^{-/-}$ and ICE$^{-/-}$ mouse livers.

Reduced Metastasis and Growth of B16M Cells Injected into IL-1β and ICE Deficient Mice Two independent experiments, one year apart, were performed using two different batches of same B16M cells intrasplenically injected in adult C57B1/6J wild-type, ICE$^{-/-}$ and IL-1β$^{-/-}$ mice. Necropsic inspection demonstrated visible melanotic tumors in the spleen from all assayed mice, without significant differences in size as evaluated by splenic weight (Table 1). In contrast, a marked decrease in metastasis occurred in IL-1β$^{-/-}$ and, specially, ICE$^{-/-}$ mouse livers compared to wild-type mouse livers (FIG. 1). A quantitative histological analysis on number and size of metastatic foci was carried out to determine metastasis density (as no. foci/100 mm$^3$) and volume (percent organ occupancy) parameters in studied mouse livers. Compared to wild-type mice (Table 1), hepatic metastasis density significantly (P<0.01) decreased in IL-1β$^{-/-}$ and ICE$^{-/-}$ mouse livers by 84%-to-90%, indicating that most of injected B16M cells were unable to implantate in hepatic tissue from these mice. In addition, metastasis volume also significantly (P<0.01) decreased in IL-1β$^{-/-}$ and ICE$^{-/-}$ mouse livers by 6-to-7-fold, as compared to values in wild-type mouse livers, indicating that B16M cells succeeding to colonize liver had also a reduced growth rate. We also observed a difference in these metastasis parameters between IL-1β$^{-/-}$ and ICE$^{-/-}$ mouse livers, leading to metastasis eradication in almost all ICE$^{-/-}$ mouse livers from experiment I (FIG. 1).

TABLE 1

Quantitative histological analysis on the experimental hepatic colonization of intrasplenically-injected B16M cells in IL-1,$^{-/-}$ and ICE$^{-/-}$ mice

| Mouse Group | Metastasis density (as no. foci/100 mm$^3$) | Metastasis volume (as % liver volume) |
|---|---|---|
| Experiment I | | |
| Wild-type mice | 234.16 ± 58.36 | 66.18% |
| IL-1,$^{-/-}$ mice | 25.18 ± 21.02* | 10.05% |
| ICE$^{-/-}$ mice | 13.56 ± 16.20* | 2.1% |
| Experiment II | | |
| Wild-type mice | 198.40 ± 100.54 | 59.62% |
| IL-1β$^{-/-}$ mice | 33.79 ± 19.89* | 9.70% |
| ICE$^{-/-}$ mice | 27.73 ± 15.68* | 8.08% |

Data represent average values ± SD from two independent experiments (7 to 15 mice per experimental group were used).
*Differences that were statistically significant (two-sided, p < 0.01) with respect to wild type mice employing the analysis of variance (ANOVA) and the Scheffe F-test, are indicated.

Example 4

Figure 2A:
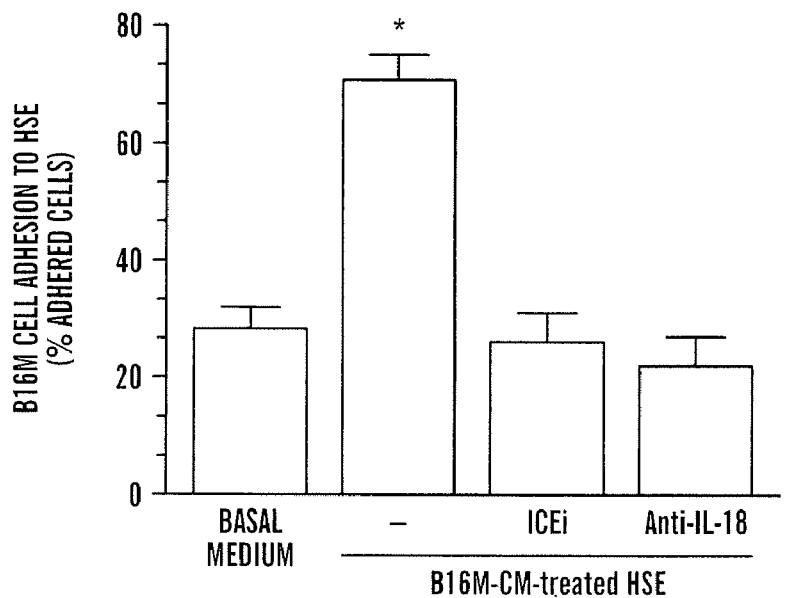
FIG. 2 Effect of irreversible ICE inhibitor and anti-mouse IL-18 antibody on B16M cell adhesion to HSE cells, and IL-1β and TNF-α production from untreated and B16M-CM-treated HSE. Cultured HSE cells were incubated in the presence of B16M-CM for 10 h. In some experiments, both untreated and treated HSE cells received 10 μM ICEi or 10
Figure 2B:
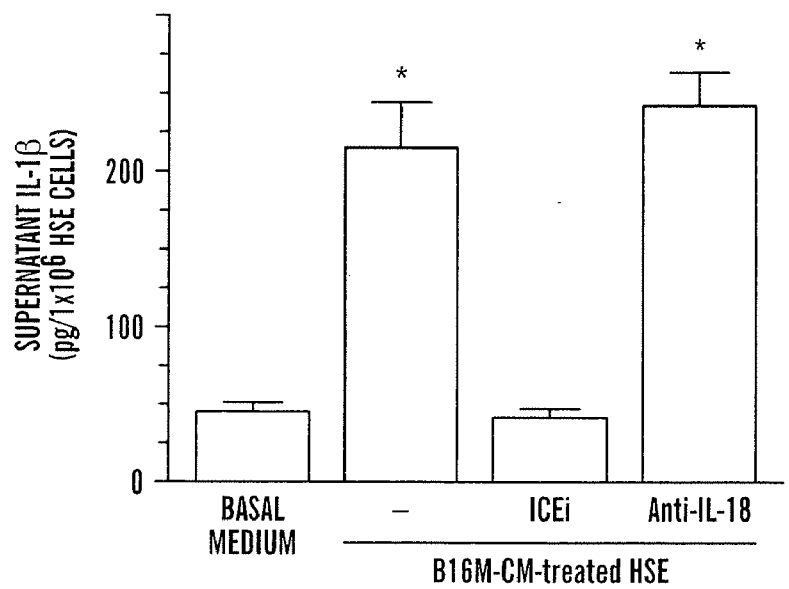
Figure 2C:
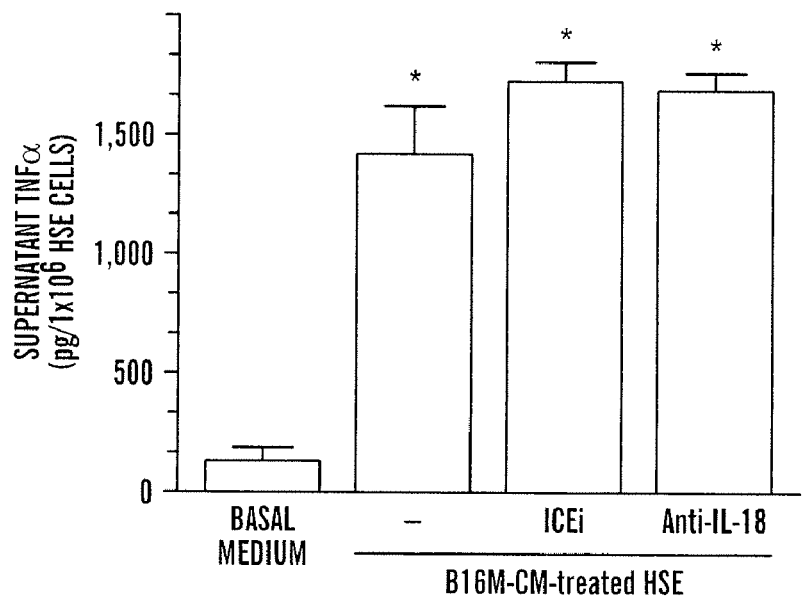

Autocrine IL-18 Mediates TNF-α- and IL-1β-Induced Adhesiveness from B16M-CM-Activated HSE B16M-CM significantly (P<0.01) increased HSE cell production of TNF-α and IL-1β, and their adhesiveness for other B16M cells in vitro (FIG. 2). Incubation of HSE with 10 μM ICEi for 18 h completely abrogated B16M-CM-induced adhesiveness without decreasing TNF-α production from HSE. Exogenously added murine IL-1β did not compensate for the blocking effect of ICEi on HSE, which is in contrast to the significant B16M cell adhesion increase in IL-1β-treated control HSE (FIG. 3). The fact that B16M-CM-induced adhesion enhancement was abolished in the presence of elevated concentrations of endogenously produced TNF-α and exogenously added IL-1β indicates that none of these cytokines directly upregulated HSE adhesiveness. Importantly, the presence of anti-murine IL-18 antibody added to HSE before stimulation with B16M-CM prevented B16M-CM-induced adhesiveness without affecting induced IL-1β and TNF-α production from HSE (FIG. 2). Moreover, anti-IL-18 antibody also prevented adhesion-stimulating effects of murine IL-1β and TNF-α on HSE (FIG. 3), indicating that proadhesive actions of these cytokines on HSE were both IL-18-mediated. RT-PCR confined that HSE cells expressed IL-18 gene (data not shown). Conversely, murine IL-18 significantly (P<0.01) increased B16M cell adhesion to HSE (FIG. 4), and neither TNF-sR p55 nor IL-1Ra were able to inhibit it, confirming that neither autocrine TNF-α nor IL-1β accounted for IL-18-induced HSE adhesiveness. However, as shown in FIG. 4, anti-VCAM-1 antibody completely inhibited adhesion of B16M cells to IL-18-treated HSE. Control non-specific IgG did not affect the upregulation of B16M cell adhesion to IL-18-treated HSE.

Example 5

IL-18BP Prevents the Adhesion of B16 Melanoma Cells Induced by B16-conditioned Medium As shown in Table 2, the addition of IL-18BP to HSE stimulated with B16-CM reduced the percent of adhering cells from 35% to 8.70% (p<0.01). This represents a 100% inhibition since the level of adhesion was below the level of adhering cells using basal medium. This result suggests that endogenous IL-18 from the HSE may be an endogenous source of IL-18 in addition to that present in the B16M-CM.

TABLE 2

Inhibitory Effect of IL-1BP on B16-conditioned medium adhesion of B16 melanoma cells to Hepatic Sinsusoidal Endothelial Cells

| | % Melanoma Cell Adhesion |
|---|---|
| Basal medium | 10.15 ± 1.5 |
| B16-CM | 35.10 ± 4.4 |
| B16-CM/IL-18BP (1 ng/ml) | 15.00 ± 2.5** |
| B16-CM/IL-18BP (10 ng/ml) | 8.70 ± 1.1** |

Data represent average values ± SD from 2 independent experiments done in sextuplicat (N = 12)
**Differences that were statistically significant (two-sided, $p < 0.01$) with respect to B16-CM employing the analysis of variance (ANOVA) and the Scheffe F-test, are indicated.

REFERENCES

1. Kohn, E. C., and Liotta, L. A. (1995) *Cancer Res* 55(9), 1856-62
2. Nicolson, G. L., and Winkelhake, J. L. (1975) *Nature* 255, 230-232
3. Freedman, A., Munro, M., Rice, G. E., Bevilacqua, M. P., Morimoto, C., McIntyre, B. W., Rhynhart, K., Pober, J. S., and Nadler, L. M. (1990) *Science* 249, 1030-1033
4. Miyake, M., Fuchimoto, S., Iwagaki, H., Matsubara, N., Edamatsu, R., Hiramatsu, M., and Orita, K. (1991) *Res. Comm. Chem. Pathol. Pharmacol.* 71, 293-307
5. Simmons, P. J., Masinovsky, B., Longenecker, B. M., Berenson, R., Torok-Storb, B., and Gallatin, W. M. (1992) *Blood* 80(2), 388-95
6. Rice, G. E., and Bevilacqua, M. P. (1989) *Science* 246, 1303-1306
7. Okahara, H., Yagita, H., Miyake, K., and Okumura, K. (1994) *Cancer Res* 54, 3233-3236
8. Garofalo, A., Chirivi, R. G. S., Foglieni, C., Pigot, R., Mortarini, R., Martin-Padura, I., Anichini, A., Gearing, A. J., Sanchez-Madrid, F., Dejana, E., and Giavazzi, R. (1995) *Cancer Res* 55, 414-419
9. Martin-Padura, I., Mortarini, R., Lauri, D., Bemasconi, S., Sanchez-Madrid, F., Panniani, G., Mantovani, A., Anichini, A., and Dejana, E. (1991) *Cancer Res* 51, 2239-2241
10. Lauri, D., Bertomeu, M.-C., and Orr, F. W. (1990) *Clin Exp Metastasis* 8, 27-32
11. Anasagasti, M. J., Alvarez, A., Martin, J. J., Mendoza, L., and Vidal-Vanaclocha, F. (1997) *Hepatology* 25, 840-846
12. Bani, M. R., Garofalo, A., Scanziani, E., and Giavazzi, R. (1991) *J. Natl. Cancer Inst.* 83, 119-123
13. Bertomeu, M. C., Gallo, S., Lauri, D., Haas, T. A., Orr, F. W., Bastida, E., and Buchanan, M. R. (1993) *Clin Exp Metastasis* 11, 243-250
14. Burrows, F. J., Haskard, D. O., Hart, I. R., Marshall, J. F., Selkirk, S., Poole, S., and Thorpe, P. E. (1991) *Cancer Res* 51, 4768-4775
15. Chirivi, R. G. S., Garofalo, A., Padura, I. M., Mantovani, A., and Giavazzi, R. (1993) *Cancer Res* 53, 5051-5054
16. Vidal-Vanaclocha, F., Amézaga, C., Asumendi, A., Kaplanski, G., and Dinarello, C. A. (1994) *Cancer Res* 54, 2667-2672
17. Vidal-Vanaclocha, F., Alvarez, A., Asumendi, A., Urcelay, B., Tonino, P., and Dinarello, C. A. (1996) *J Natl Cancer Inst* 88, 198-205
18. Malik, S. T., Naylor, M. S., East, N., Oliff, A., and Balkwill, F. R. (1990) *Eur J Cancer* 26, 1031-1034
19. Orosz, P., Echtenacher, B., Falk, W., Ruschoff, J., Weber, D., and Mannel, D. N. (1993) *J Exp Med* 177, 1391-1398
20. Orosz, P., Krüger, A., Hubbe, M., Rüschoff, J., Von Hoegen, P., and Männel, D. N. (1995) *Int. J. Cancer* 60, 867-871
21. Mendoza, L., Olaso, E., Anasagasti, M. J., Fuentes, A., and Vidal-Vanaclocha, F. (1998) *J Cell Physiol* 174, 322-330
22. Bazan, J. F., Timans, J. C., and Kastelein, R. A. (1996) *Nature* 379(6566), 591
23. Okamura, H., Tsutsui, H., Komatsu, T., Yutsudo, M., Hakura, A., Tanimoto, T., Torigoe, K., Okura, T., Nukada, Y., Hattori, K., Akita, K., Namba, M., Tanabe, F., Konishi, K., Fukuda, S., and Kurimoto, M. (1995) *Nature* 378, 88-91
24. Tsutsui, H., Matsui, K., Kawada, N., Hyodo, Y., Hayashi, N., Okamura, H., Higashino, K., and Nakanishi, K. (1997) *J Immunol* 159(8), 3961-7
25. Puren, A. J., Fantuzzi, G., Gu, Y., Su, M. S.-S., and Dinarello, C. A. (1998) *J Clin Invest* 101, 711-724
26. Vidal-Vanaclocha, F., Rocha, M., Asumendi, A., and Barbera-Guillem, E. (1993) *Hepatology* 18, 328-339
27. Fantuzzi, G., Puren, A. J., Harding, M. W., Livingston, D. J., and Dinarello, C. A. (1998) *Blood* 91, 2118-2125
28. Novick, D., Kim, S-H., Fantuzzi, G., Reznikov, L. L., Charles A. Dinarello, C. A., and Rubinstein, M. (1999) *Immunity* 10, 127-136.

The invention claimed is:

1. A method of inhibiting melanoma cell hepatic and lung tissue metastasis in a subject in need thereof comprising administering to the subject a therapeutically effective amount of IL-18BP in a pharmaceutically acceptable carrier.

\* \* \* \* \*